(12) United States Patent
Martin et al.

(10) Patent No.: US 9,259,715 B2
(45) Date of Patent: Feb. 16, 2016

(54) HYDROGENOLYSIS CATALYSTS AND USES THEREOF

(71) Applicant: ARCHER DANIELS MIDLAND COMPANY, Decatur, IL (US)

(72) Inventors: Kevin Martin, Mt. Zion, IL (US); Josh Terrian, Lovington, IL (US); Leandra Vircks, Clinton, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 14/436,372

(22) PCT Filed: Oct. 16, 2013

(86) PCT No.: PCT/US2013/065167
§ 371 (c)(1),
(2) Date: Apr. 16, 2015

(87) PCT Pub. No.: WO2014/062757
PCT Pub. Date: Apr. 24, 2014

(65) Prior Publication Data
US 2015/0290628 A1    Oct. 15, 2015

Related U.S. Application Data

(60) Provisional application No. 61/714,821, filed on Oct. 17, 2012.

(51) Int. Cl.
*B01J 23/889* (2006.01)
*B01J 35/00* (2006.01)
*C07C 29/60* (2006.01)
*B01J 21/18* (2006.01)
*B01J 37/16* (2006.01)

(52) U.S. Cl.
CPC ............. *B01J 23/8896* (2013.01); *B01J 21/18* (2013.01); *B01J 35/0006* (2013.01); *B01J 37/16* (2013.01); *C07C 29/60* (2013.01)

(58) Field of Classification Search
None
See application file for complete search history.

(56) References Cited

U.S. PATENT DOCUMENTS

| | | | |
|---|---|---|---|
| 4,401,823 A | 8/1983 | Arena | |
| 7,230,141 B2 | 6/2007 | Bottke et al. | |
| 8,187,997 B2 * | 5/2012 | King ................. | B01J 21/12 502/207 |
| 2005/0032627 A1 | 2/2005 | Bottke et al. | |
| 2008/0103339 A1 | 5/2008 | Bloom | |
| 2009/0088317 A1 * | 4/2009 | Frye, Jr. ................. | C07C 29/60 502/178 |
| 2009/0264687 A1 | 10/2009 | Holladay et al. | |
| 2010/0255983 A1 | 10/2010 | Zhang | |
| 2010/0274053 A1 | 10/2010 | Siegel et al. | |
| 2012/0238780 A1 * | 9/2012 | King ................. | B01J 21/12 564/470 |

OTHER PUBLICATIONS

Copenheaver, Blaine R., International Search Report and Written Opinion, mail date Feb. 21, 2014, pp. 1-15, USPTO, USA (PCT application No. PCT/US2013/065167).

* cited by examiner

*Primary Examiner* — Brian J Davis
(74) *Attorney, Agent, or Firm* — Andrew F. Nilles; Alexandra Lakshmanan

(57) ABSTRACT

A hydrogenation catalyst comprising nickel, rhenium, and cadmium is disclosed. Process of using hydrogenation catalyst for producing propylene glycol from polyol feedstock are also disclosed. The present invention relates generally to catalysts and more particularly, to catalysts having an enhanced ability to produce propylene glycol from sugar alcohols while reducing the production of by-products.

19 Claims, 1 Drawing Sheet

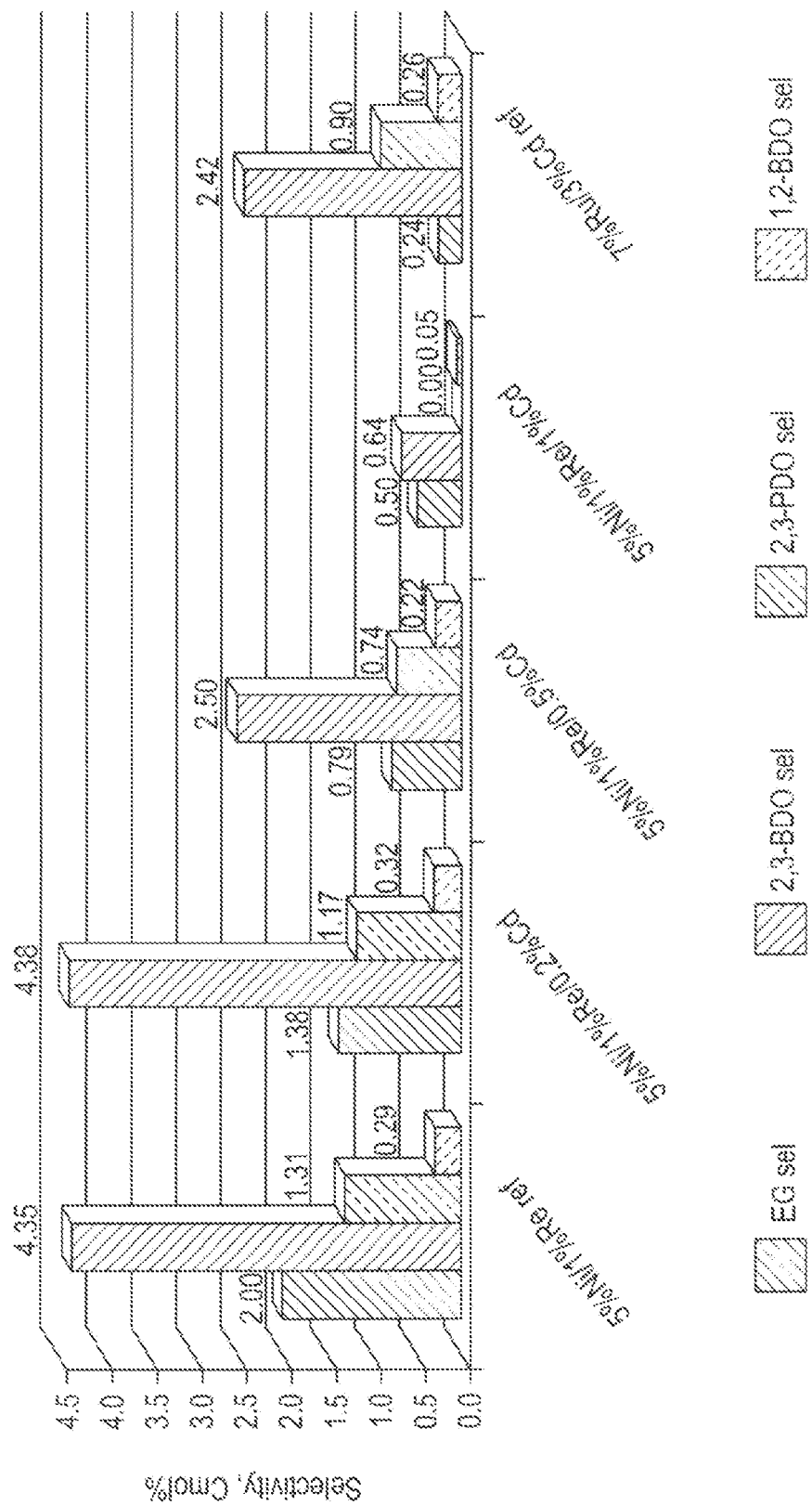

HYDROGENOLYSIS CATALYSTS AND USES THEREOF

CROSS-REFERENCE TO RELATED APPLICATIONS

This application is a national stage entry of International Application No. PCT/US2013/65167, filed Oct. 16, 2013, which itself claims priority to U.S. Provisional Patent Application No. 61/714,821, filed Oct. 17, 2012, each of the contents of the entirety of which are incorporated by this reference.

TECHNICAL FIELD

The present invention relates generally to catalysts and more particularly, to catalysts having an enhanced ability to produce propylene glycol from sugar alcohols while reducing the production of by-products.

BACKGROUND OF THE INVENTION

Propylene glycol can be produced by the catalytic hydrogenolysis of sugar alcohols. Commercially, propylene glycol is produced from glycerol. The hydrogenolysis reaction is effectuated by catalysts such as those described in US Patent Application Publication 2009/0088317.

The hydrogenolysis reaction used to create propylene glycol results in the production of side products such as ethylene glycol, 2,3-butanediol, 1,2-butanediol, 1,3-butanediol, 1,4-butanediol, 2,3-pentanediol, and 2,4-pentanediol. However, these diols and the ethylene glycol are difficult to separate from the propylene glycol, and one isomer of the 2,3-pentanediol cannot be economically separated from propylene glycol by distillation. While it is possible to reduce the production of such diols by varying the hydrogenolysis reactions, such variances may reduce the overall productivity of the propylene glycol process.

Methods have been developed to isolate or purify the propylene glycol from these diols and/or the ethylene glycol. U.S. Pat. No. 8,143,458, assigned to Archer-Daniels-Midland Company, discloses processes for producing propylene glycol and separating the unwanted diols from the propylene glycol. While such processes are able to effectively separate the diols from the propylene glycol, such processes are time consuming and expensive.

Thus, needs exist for the more efficient production of propylene glycol from sugar alcohols.

SUMMARY OF THE INVENTION

In each of its various embodiments, the present invention fulfills these needs. In one embodiment, the present invention discloses a catalyst that may be used in a hydrogenolysis reaction where the catalyst provides an enhanced selectivity to propylene glycol at a greater conversion, with a reduced production of ethylene glycol and diols. The invention results in a greater productivity of propylene glycol in the resulting product mixture, an enhanced recovery of propylene glycol from the product mixture, and reduced costs in separating pure propylene glycol from the product mixture.

In another embodiment, a hydrogenation catalyst comprises Ni, Re, and Cd.

In an additional embodiment, a process for producing propylene glycol comprises placing a polyol feedstock in contact with a catalyst comprising Ni, Re, and Cd such that the propylene glycol is formed.

In a further embodiment, a catalyst for hydrogenation of a polyol feedstock to produce propylene glycol comprises a support material and catalytic metal components comprising Ni, Re, and Cd.

DESCRIPTION OF THE DRAWINGS

FIG. 1 is a graphical representation of the improved selectivity of various embodiments of catalysts of the present invention for producing propylene glycol.

DETAILED DESCRIPTION OF THE INVENTION

In one embodiment, the present invention discloses catalysts for the hydrogenation of sugar alcohols, such as glycerol, to produce propylene glycol. In another embodiment, the present invention discloses a process for the hydrogenolysis of polyols with an improved selectivity for propylene glycol, while reducing the formation of ethylene glycol and diols.

In the present application, including the claims, other than in the operating examples or where otherwise indicated, all numbers expressing quantities or characteristics are to be understood as being modified in all instances by the term "about". Unless indicated to the contrary, any numerical parameters set forth in the following description may vary depending on the desired properties in the compositions and methods according to the present disclosure. At the very least, and not as an attempt to limit the application of the doctrine of equivalents to the scope of the claims, each numerical parameter described in the present description should at least be construed in light of the number of reported significant digits and by applying ordinary rounding techniques.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, the disclosure set forth herein supersedes any conflicting material incorporated herein by reference.

In one embodiment, the present invention provides catalysts and uses thereof for hydrogenolysis of polyols which maximize the selectivity of the reaction towards the formation of propylene glycol, while minimizing the formation of other polyols. In a further embodiment, the catalyst comprises metal catalyst components including nickel (Ni), rhenium (Re), and cadmium (Cd). In one embodiment, the catalyst comprises 3-7% by weight Ni, 0.2-1.8% by weight Re, 0.2-3.0% by weight Cd, or combinations of any thereof. In a further embodiment, the catalyst comprises 4.5-5.5% by weight Ni, 0.5-1.5% by weight Re, 0.75-2.0% by weight Cd, or combinations of any thereof. In an additional embodiment, the metal catalyst components consist of the Ni, Re, and Cd.

In one embodiment, the metal catalyst components may be impregnated on the support material in salt form. In other embodiments, the metal catalyst components may be impregnated on the support material in oxide or element form as well.

In another embodiment, reaction conditions of the hydrogenolysis reaction using the catalysts of the present invention are provided that effectively convert polyol feedstocks to propylene glycol. In one embodiment, the reaction conditions of the hydrogenolysis reaction may be varied to optimize the performance of the catalysts of the present invention for the selective formation of propylene glycol. Such optimized conditions are able to produce propylene glycol with little or negligible formation of other polyols that are difficult to separate from the propylene glycol by distillation.

In an additional embodiment, a process is provided for hydrogenolysis of glycerol comprising placing glycerol in contact with hydrogen and a catalyst of the present invention at a liquid hourly space velocity of 0.5 hr$^{-1}$ to 10.0 hr$^{-1}$ to minimize the formation of diols.

In a further embodiment, a process for hydrogenolysis of polyol feedstocks to minimize the formation of butanediols comprises adding a base to the reaction. The base may be selected from the group consisting of alkali metal hydroxides, alkaline earth metal oxides, alkoxides, hydroxides, and basic salts. The base may be added at amounts varying between 0.01 to 2.5 weight percent of the polyol feedstock.

In yet a further embodiment, the process for hydrogenolysis of a polyol feedstock may be conducted at a reaction temperature of 178-205° C. in order to minimize the formation of butanediols. In yet a further embodiment, the reaction temperature may be 195-205° C.

In an additional embodiment, the process for hydrogenolysis of polyols using the catalyst of the present invention, while minimizing the formation of butanediols, comprises mixing a polyol containing material with a base to produce a hydrogenolysis precursor mixture, subjecting the hydrogenolysis precursor mixture to a condition that allows the propylene glycol to form, wherein the condition is selected from the group consisting of liquid hourly space velocity, temperature, pressure, the presence of a catalyst and any combinations thereof. In a further embodiment, the propylene glycol may be isolated and other polyhydric alcohols are removed from the propylene glycol.

In one embodiment, the polyol feedstock used in the present invention may be bio-derived and can be obtained by subjecting sugars or carbohydrates to hydrogenolysis (also called catalytic cracking). In one embodiment, sorbitol may be subjected to hydrogenolysis to provide a mixture comprising bio based polyols such as described in "Hydrogenolysis of sorbitol." Clark, I., *J. Ind. Eng. Chem.* (Washington, D.C.) (1958), 50, 1125-6, the disclosure of which is incorporated by reference herein in its entirety). According to other embodiments, other polysaccharides and polyols suitable for hydrogenolysis include, but are not limited to, glucose (dextrose), sorbitol, mannitol, sucrose, lactose, maltose, alpha-methyl-d-glucoside, pentaacetvylglucose, gluconic lactone, and any combination thereof (see, e.g. "Hydrogenolysis of sugars." Zartman, W. and Adkins. H., *J. Amer. Chem. Soc.* (1933) 55, 4559-63, the disclosure of which is incorporated by reference herein in its entirety).

In a further embodiment, the hydrogenolysis product may comprise a mixture of propylene glycol and ethylene glycol, along with minor amounts of one or more of methanol, 2-propanol, glycerol, lactic acid, glyceric acid, sodium lactate, and sodium glycerate. Several butanediols (BDO) such 1,2-butanediol, 1,3-butanediol, 1,4-butanediol, and 2,3-butanediol may also be produced in addition to 2,4-pentanediol (2,4-PeDO).

In various embodiments, the hydrogenolysis product of the present invention comprising the propylene glycol may be used in a composition including, but not limited to, a deicer, an antifreeze, a resin, a laundry detergent, a soap, a personal care product, a cosmetic product, a pharmaceutical product, or as a food ingredient in a foodstuff or beverage.

In another embodiment, the feedstock for the hydrogenolysis is glycerol. In an embodiment, the glycerol feed stock includes a diluent, such as water, or a non-aqueous solvent. Non-aqueous solvents that may be used include, but are not limited to, methanol, ethanol, ethylene glycol, propylene glycol, n-propanol, and iso-propanol. Glycerol feed stocks are commercially available, or can be obtained as a byproduct of commercial biodiesel production. According to other embodiments, the polyol feedstock may be a side product or co-product from the synthesis of bio-diesel or the saponification of vegetable oils and/or animal fats (i.e., triacylglycerols). For instance, the glycerol feed stocks may be obtained through fats and oils processing or generated as a byproduct in the manufacture of soaps. The feed stock may for example, be provided as glycerol byproduct of primary alcohol alcoholysis of a glyceride, such as a mono-, di- or tri glyceride. These glycerides may be obtained from refining edible and non-edible plant feed stocks including without limitation butterfat, cocoa butter, cocoa butter substitutes, illipe fat, kokum butter, milk fat, mowrah fat, phulwara butter, sal fat, shea fat, borneo tallow, lard, lanolin, beef tallow, mutton tallow, tallow, animal fat, canola oil, castor oil, coconut oil, coriander oil, corn oil, cottonseed oil, hazelnut oil, hempseed oil, jatropha oil, linseed oil, mango kernel oil, meadowfoam oil, mustard oil, neat's foot oil, olive oil, palm oil, palm kernel oil, peanut oil, rapeseed oil, rice bran oil, safflower oil, sasanqua oil, shea butter, soybean oil, sunflower seed oil, tall oil, tsubaki oil, tung oil, vegetable oils, marine oils, menhaden oil, candlefish oil, cod-liver oil, orange roughy oil, pile herd oil, sardine oil, whale oils, herring oils, triglyceride, diglyceride, monoglyceride, triolein palm olein, palm stearin, palm kernel olein, palm kernel stearin, triglycerides of medium chain fatty acids, and derivatives, conjugated derivatives, genetically-modified derivatives, and mixtures of any thereof:

Glycerol feedstocks are known to those of ordinary skill in the art and can be used either in pure or crude form. The purity of United States Pharmacopeia (USP) grade glycerol is greater than 99%. However, the purity of the glycerol having utility in the present invention may be between 10-99% by weight of the feedstock. The glycerol may also contain other constituents such as water, triglycerides, free fatty acids, soap stock, salt, and unsaponifiable matter. In one embodiment, the feedstock may comprise 20-80% by weight of the glycerol.

In a further embodiment, catalysts for the present hydrogenolysis processes may be solid or heterogeneous catalysis. The catalyst support material may include those known in the art or as described herein. The catalysts are provided with a large surface area support material that prevents degradation under the reaction conditions. In one embodiment, the surface area may be a BET surface area between 1 to 1,000 m$^2$ per gram and in an additional embodiment, the surface area may be a BET surface area between 400 to 1,000 m$^2$ per gram. These support materials may include, but are not limited to, carbon, alumina, titania, zirconia, silica, or a combination thereof. These support materials can also be prepared in mixed or layered materials such as mixed with catalyst materials.

Catalytic hydrogenolysis of a polyol feedstock to produce propylene glycol can further comprise utilization of an added base. Assuming a neutral starting pH of a polyol feedstock, such as sorbitol or glycerol, of from about pH 5 to about pH 8, an appropriate pH for catalytic hydrogenolysis can be achieved by, for example, an addition an alkali, such as sodium hydroxide, to a final concentration of from about 0% to about 10% by weight, or from about 0.5% to about 2% by weight, relative to the weight of the final solution. In an embodiment, the selectivity of the catalyst and yield of propylene glycol (PG) can be improved by treating the reactant mixture to render the pH value neutral or alkali prior to or during the hydrogenolysis reaction, as well as carrying out the reaction under alkaline conditions. During the reaction, organic acids are formed which neutralize the alkali added to the reaction. As the reaction proceeds, the pH is reduced, causing concomitant reduction in the selectivity of the catalyst. Methods are provided in the present disclosure to ensure that the reaction is carried out in sufficient alkalinity to ameliorate this problem. In one embodiment, the reaction is conducted under alkali conditions, such as at a pH 8 to 14, or at a pH of 10 to 13. These pH values may be obtained by adding an alkali, such as a strong base such as sodium hydroxide. In embodiments, the sodium hydroxide could be added to a level of 0.2 to 1.0%.

The temperature used in the hydrogenolysis reaction may range from 150° C. to 300° C. and the pressure may range from between 500 psi and 2000 psi or 1000 psi to 1600 psi. The reaction time for the hydrogenolysis reaction is defined by the term "weight hourly space velocity" (WHSV) which is the weight of reactant per unit weight of catalyst per hour. Alternatively, the term "liquid hourly space velocity" (LHSV) may also be used, and is volume of reactant per unit volume of catalyst per hour. In an embodiment, a value for HSV is 1.8, which can be modified suitably to meet reactor design specifications using techniques well known to those in the art.

The compositions and methods disclosed herein are not limited to any particular hydrogenolysis procedures, reagents, or catalysts. Rather, the compositions and methods described herein may incorporate hydrogenolysis products from any known method.

Hydrogenolysis of a polyol feedstock such as, for example, a bio-derived polyol feedstock as described herein, results in a hydrogenolysis product. According to certain embodiments, the hydrogenolysis product may comprise a mixture of propylene glycol and ethylene glycol containing minor amounts of one or more of methanol, 2-propanol, glycerol, lactic acid, glyceric acid, sodium lactate, sodium glycerate, and combinations of any thereof.

Propylene glycol produced by the embodiments described herein may be referred to as "bio-based" propylene glycol. Propylene glycol produced as such finds many uses. Some of these include, but are not limited to, use as a solvent for aromatics in the flavor-concentrate industry; a wetting agent for natural gums; an ingredient in the compounding of citrus and other emulsified flavors; a solvent in elixirs and pharmaceutical preparations; a solvent and coupling agent in the formulation of sunscreen lotion shampoos, shaving creams, and other similar products; an emulsifier in cosmetic and pharmaceutical creams; an ingredient for low-temperature heat-transfer fluids, involving indirect food contacts, such as brewing and dairy uses, as well as refrigerated grocery display cases; a humectant, preservative, and stabilizer in semi-moist pet food, bakery goods, food flavorings, and salad dressings; use as a dust suppression agent; solvents and compatibilizers for dyes, resins, and inks used in modern high-speed printing presses; surface lubricant in metal part manufacture; as a raw material for dipropylene glycol phthalate; a plasticizer for polyvinyl chloride (PVC) resins; for use in the natural gas processing industry; and to provide freeze-thaw protection in various wax products to help prevent damaged caused by freezing. Propylene glycol may also be used as the starting material for the synthesis of propylene glycol esters with sorbitol and/or fatty acids. Such uses are not limited or all inclusive and may be readily developed by those skilled in the art.

Various embodiments of the present disclosure relate to a bio-based propylene glycol and ethylene glycol. The products produced by the processes of the present invention produced by the hydrogenolysis of bio-derived polyols and the products produced therefrom may be differentiated from petroleum derived products, for example, by their carbon isotope ratios using ASTM International Radioisotope Standard Method D 6866. Products produced from the product mixture of the hydrogenolysis product from a bio-derived polyol feedstock may have a bio-based carbon isotope ratio ranging from 50% to 100. As used herein the term "bio-based carbon isotope ratio" includes a composition or a component of a composition having a carbon isotope ratio, as determined, for example, by ASTM International Radioisotope Standard Method D 6866, the disclosure of which is incorporated by reference herein in its entirety, that is indicative of a composition including, in whole or in significant part, of biological products or renewable agricultural materials (including plant, animal and marine materials) or forestry materials (Method ASTM 6866).

The following exemplary, non-limiting examples are provided to further describe the embodiments presented herein. Those having ordinary skill in the art will appreciate that variations of these Examples are possible within the scope of the present invention.

Example 1

The effect of an additional metal with Ni/Re activated carbon catalysts for converting glycerol to propylene glycol was evaluated. Catalysts were prepared by impregnating 200 mg aliquots of NORIT ROX 0.8 brand activated carbon, available from Norit Americas Inc., Marshall Tex., with mixed metal solutions. The activated carbon was prepared with 5% by weight of the catalyst of Ni, 1% by weight of the catalyst of Re, and Cd at levels of 0.2%, 0.5%, 0.75%, 1.0%, 1.25%, 1.5%, 1.75%, and 2.0% by weight of the catalyst. Cadmium(II) nitrate tetrahydrate was used for Cd. Mixed solutions of the proper ratios of nickel ill nitrate for Ni, perrhenic acid for Re, and cadmium(II) nitrate tetrahydrate for Cd were impregnated on the activated carbon with the volumes of such solutions to achieve the desired amounts of metal on the catalyst. The total volume of the mixed solutions was added to the activated carbon in five aliquots with constant agitation by vibratory plate and mechanical mixing with an overhead stirrer between aliquots.

The impregnated carbons were transferred to stainless steel reaction vessels with 24-well plates. In addition to the Ni/Re/Cd catalysts, the catalysts 5% Ni/1% Re and 7% Ru/3% Cd were added to 2 vessels each as references. The plates were sealed in gas treatment reactors, placed in box furnaces with 5% hydrogen gas attached to the reactors, brought to 330° C. at 5°/minutes, held for 4 hours, and cooled. The reactors were sealed, brought into an oxygen-free glove box, and opened. The reaction vessels were transferred to a plate suitable for use in a screening pressure reactor.

A mixed feed of 40% glycerol and 1% NaOH in water was dispensed into each reactor (2 mL). Catalytic reactions were carried out in sealed hydrogenation reactors at 180° C. at 1200 psi hydrogen pressure for 2 hours. Products of the reaction were analyzed by gas chromatography which showed enhanced selectivity for propylene glycol and a minimized production of by-product diols as compared to the reference catalysts. The results of this reaction are presented in Table 1.

A graphical representation of the improved selectivity of the catalysts of the present invention is shown in FIG. 1. In FIG. 1, the bars in the graph from left to right for each catalyst represent EG selectivity, 2,3-BDO selectivity, 2,3-PDO selectivity, and 1,2-BDO selectivity, respectively.

TABLE 1

| Cadmium level, Wt % | Glycerol Conversion % | PG sel. Cmol % | EG sel. Cmol % | 2,3-BDO sel., Cmol % | 2,3-PeDO sel., Cmol % | 1,2-BDO sel., Cmol % |
|---|---|---|---|---|---|---|
| 0% (Ni/Re ref.) | 39.73 | 75.04 | 1.94 | 4.38 | 1.33 | 0.30 |
| 0.2% | 35.42 | 71.13 | 1.38 | 4.38 | 1.17 | 0.32 |
| 0.5% | 39.25 | 75.73 | 0.79 | 2.50 | 0.74 | 0.22 |
| 0.75% | 43.57 | 79.30 | 0.70 | 1.45 | 0.32 | 0.17 |
| 1.0% | 44.72 | 80.38 | 0.52 | 0.75 | n.d. | 0.04 |
| 1.25% | 44.95 | 81.58 | 0.38 | 0.42 | n.d. | 0.07 |
| 1.5% | 43.52 | 80.76 | 0.26 | 0.13 | n.d. | 0.10 |
| 1.75% | 40.05 | 82.85 | 0.14 | 0.14 | n.d. | 0.11 |
| 2.0% | 40.66 | 80.65 | 0.06 | n.d. | n.d. | 0.11 |
| 3.0 (Ru/Cd ref.) | 41.94 | 72.84 | 0.28 | 2.34 | 0.89 | 0.25 | n.d. means not detected.

Example 2

30 gram batches of Ni/Re/Cd catalyst were prepared using NORIT ROX 0.8 brand activated carbon, available from Norit Americas Inc., Marshall IX. The catalysts were prepared by the incipient wetness of a mixed nickel nitrate, perrhenic acid, and cadmium nitrate solution mixed with the activated carbon. The resulting material was dried in a vacuum oven at 80° C. for 40 hours. Three catalysts were prepared: 5% Ni/1% Re/1% Cd, 5% Ni/1% Re/1.25% Cd, and 5% Ni/1% Re/2% Cd.

The three catalysts were evaluated for their ability to convert glycerol to propylene glycol. The three catalysts were loaded in 30 cc reactors and reduced by hydrogen in-situ flow for between 4-16 hours at 320° C. before use. The following conditions were used for the hydrogenolysis reaction: reaction jacket temperature of 190° C.-205° C.; a hydrogen pressure of 1800 psi; a hydrogen flow (STP) of 1 L/minute; a liquid hourly space velocity (LHSV) of $0.7\,hr^{-1}$-$1.0\,hr^{-1}$ (feed rate 0.35 mL/min-0.5 mL/min). The feed composition was 40 wt % glycerol and 0.5-1 wt % NaOH in deionized water. The product samples were analyzed by HPLC and GC at various sampling times during the reaction. The results are presented in Tables 2-4.

TABLE 2

5% Ni/1% Re/1% Cd catalyst.

| Temp. °C. | wt % NaOH | LHSV $hr^{-1}$ | % Conv. | wt % PG yld. | Cmol % PG sel. | Cmol % EG sel. | Cmol % 2,3-BDO sel. | Cmol % 2,3-PeDO sel. |
|---|---|---|---|---|---|---|---|---|
| 190 | 1.0 | 0.7 | 96.20 | 74.02 | 93.12 | 3.32 | 0.24 | 0.04 |
| 195 | 0.5 | 0.7 | 91.78 | 71.23 | 93.89 | 3.23 | 0.19 | 0.03 |
| 200 | 0.5 | 1.0 | 91.82 | 70.42 | 92.82 | 3.85 | 0.42 | 0.07 |
| 200 | 0.5 | 0.7 | 96.92 | 74.44 | 93.58 | 3.97 | 0.41 | 0.07 |

TABLE 3

5% Ni/1% Re/1.25% Cd.

| Temp. °C. | wt % NaOH | LHSV $hr^{-1}$ | % Conv. | wt % PG yld. | Cmol % PG sel. | Cmol % EG sel. | Cmol % 2,3-BDO sel. | Cmol % 2,3-PeDO sel. |
|---|---|---|---|---|---|---|---|---|
| 195 | 1.0 | 1.0 | 86.63 | 65.52 | 91.53 | 2.62 | 0.34 | 0.03 |
| 200 | 0.5 | 0.7 | 88.83 | 70.06 | 95.45 | 3.24 | 0.21 | n.d. |
| 205 | 0.5 | 1.0 | 86.14 | 66.53 | 93.47 | 3.32 | 0.28 | 0.03 |
| 205 | 0.5 | 0.7 | 91.96 | 71.76 | 94.44 | 3.63 | 0.50 | 0.09 |

TABLE 4

5% Ni/1% Re/2% Cd.

| Temp. °C. | wt % NaOH | LHSV $hr^{-1}$ | % Conv. | wt % PG yld. | Cmol % PG sel. | Cmol % EG sel. | Cmol % 2,3-BDO sel. | Cmol % 2,3-PeDO sel. |
|---|---|---|---|---|---|---|---|---|
| 195 | 1.0 | 1.0 | 84.08 | 62.64 | 90.18 | 2.18 | 0.14 | 0.02 |
| 200 | 1.0 | 1.0 | 88.27 | 66.39 | 91.03 | 2.73 | 0.25 | 0.03 |
| 205 | 0.5 | 1.0 | 88.72 | 68.64 | 93.64 | 3.00 | 0.22 | 0.04 |
| 205 | 0.5 | 0.7 | 95.66 | 74.73 | 94.54 | 3.25 | 0.32 | 0.06 |

Example 3

The performance of a Ni/Re/Cd catalyst of the present invention for converting glycerol to propylene glycol was compared with existing catalysts for converting glycerol to propylene glycol and the comparisons are shown in Table 5B. The catalysts were prepared substantially as described herein, the hydrogenolysis was performed substantially as described herein, and the reaction conditions and results are shown in the following Tables.

TABLE 5A

Run conditions.

| catalyst | Feed | | Jacket temp. | Pressure | | H2 Flow |
| | Glycerol % | NaOH % | ° C. | PSI | LHSV | ml/min. |
| --- | --- | --- | --- | --- | --- | --- |
| 7% Ru/3% Cd on carbon | 40 | 1 | 205 | 1800 | 1 | 1000 |
| 7% Ru/3% Cd on carbon | 40 | 0.5 | 205 | 1800 | 1 | 1000 |
| 7% Ru/3% Cd on carbon | 40 | 0.5 | 205 | 1800 | 0.7 | 1000 |
| 5% Ni/1% Re/1% Cd on carbon | 40 | 1 | 195 | 1800 | 0.7 | 1000 |
| 5% Ni/1% Re | 40 | 1 | 205 | 1800 | 1 | 1000 |
| 5% Ni/1% Re | 40 | 0.33 | 205 | 1800 | 0.7 | 1000 |

TABLE 5B

Results.

| catalyst | Glycerol conversion | PG yield | PG | EG | 2,3-BDO | 1,2-BDO | 2,3-PeDO | lactic acid |
| --- | --- | --- | --- | --- | --- | --- | --- | --- |
| 7% Ru/3% Cd on carbon | 90.87 | 66.71 | 88.85 | 2.37 | 0.48 | 0.12 | 0.13 | 5.72 |
| 7% Ru/3% Cd on carbon | 88.68 | 67.05 | 91.51 | 2.42 | 0.19 | 0.05 | 0.06 | 3.28 |
| 7% Ru/3% Cd on carbon | 95.11 | 72.36 | 92.08 | 2.38 | 0.31 | 0.1 | 0.13 | 3.2 |
| 5% Ni/% Re/1% Cd on carbon | 95.22 | 72.39 | 92.02 | 3.20 | 0.32 | 0.08 | 0.06 | 4.74 |
| 5% Ni/1% Re | 94.3 | 67.7 | 86.8 | 5.11 | 1.56 | 0.24 | 0.38 | 2.22 |
| 5% Ni/1% Re | 87.48 | 66.25 | 91.65 | 4.47 | 0.49 | 0.1 | 0.1 | 2.13 |

The PG selectivity of the Ni/Re/Cd catalyst of the present invention performs as better as or better than the Ru/Cd or Ni/Re catalysts by either functioning substantially the same as the known catalysts, but at a lower temperature, or by having higher PG selectivity and a lower amount of unwanted diols as compared to the known catalysts.

This disclosure has been described with reference to certain exemplary embodiments, compositions and uses thereof. However, it will be recognized by those of ordinary skill in the art that various substitutions, modifications, or combinations of any of the exemplary embodiments may be made without departing from the spirit and scope of the disclosure. Thus, the disclosure is not limited by the description of the exemplary embodiments but rather by the appended claims as originally filed.

What is claimed is:

1. A hydrogenation catalyst comprising:
   Ni;
   Re; and
   Cd.

2. The hydrogenation catalyst of claim 1, further comprising a support material.

3. The hydrogenation catalyst of claim 2, wherein the support material is selected from the group consisting of a carbon based support material, activated carbon, zirconium oxide, titanium oxide, niobium oxide, tin oxide, lanthanum oxide, tungsten oxide, silicon carbide, silicon oxycarbide, titanium carbide, titanium oxycarbide, zirconium oxycarbide, tungsten carbide, tungsten oxycarbide, and combination of any thereof.

4. The hydrogenation catalyst of claim 1, wherein:
   the Ni is present at 3-7% by weight of the hydrogenation catalyst.

5. The hydrogenation catalyst of claim 1, wherein the Re is present at 0.2-1.8% by weight of the hydrogenation catalyst.

6. The hydrogenation catalyst of claim 1, wherein the Cd is present at 0.2-3.0% by weight of the hydrogenation catalyst.

7. A process for producing propylene glycol, the process comprising:
   placing a polyol feedstock in contact with a catalyst comprising Ni, Re, and Cd; and
   placing hydrogen in contact with the polyol feedstock and the catalyst such that the propylene glycol is formed.

8. The process of claim 7, further comprising placing a base in contact with the polyol feedstock.

9. The process of claim 7, wherein the polyol feedstock is selected from the group consisting of glucose, sorbitol, mannitol, sucrose, lactose, maltose, alpha-methyl-d-glucoside, pentaacetylglucose, gluconic lactone, glycerol, and combinations of any thereof.

10. The process of claim 7, wherein the polyol feedstock is placed in contact with the catalyst at a liquid hourly space velocity of between 0.5 hr$^{-1}$ to 10.0 hr$^{-1}$.

11. The process of claim 8, wherein the base is selected from the group consisting of alkali metal hydroxides, alkoxides and basic salts and alkaline earth metal oxides, alkoxides, hydroxides, basic salts, and combinations of any thereof.

12. The process of claim 7, further comprising maintaining a reaction temperature of between 178-205° C.

13. The process of claim 7, further comprising isolating the propylene glycol.

14. The process of claim 7, further comprising maintaining a reaction temperature of between 198-205° C.

15. A catalyst for hydrogenation of a polyol feedstock to produce propylene glycol, comprising:
 a support material; and
 catalytic metal components comprising Ni, Re, and Cd.

16. The catalyst of claim 15, wherein the support material comprises carbon.

17. The catalyst of claim 15, wherein the Ni is present at 4.5-5.5% by weight.

18. The catalyst of claim 15, wherein the Re is present at 0.5-1.5% by weight.

19. The catalyst of claim 15, wherein the Cd is present at 0.75-2.0% by weight.

* * * * *